United States Patent [19]

Hicks et al.

[11] Patent Number: 5,466,771

[45] Date of Patent: Nov. 14, 1995

[54] COATING COMPOSITIONS BASED ON ALDIMINES AND POLYISOCYANATES CONTAINING ALLOPHANATE GROUPS

[75] Inventors: Sharon D. Hicks, Pittsburgh; Douglas A. Wicks, Mt. Lebanon; John H. Hunter, Coraopolis, all of Pa.

[73] Assignee: Bayer Corporation, Pittsburgh, Pa.

[21] Appl. No.: 171,281

[22] Filed: Dec. 21, 1993

[51] Int. Cl.$^6$ ............................................. C08G 18/32
[52] U.S. Cl. ................ 528/64; 528/62; 528/67; 528/59; 528/230; 252/189.21; 252/189.22; 428/423.1; 428/425.3
[58] Field of Search ....................... 528/64, 62, 67, 528/59, 230; 252/182.21, 182.22; 428/423.1, 425.3

[56] References Cited

U.S. PATENT DOCUMENTS

| | | | |
|---|---|---|---|
| 3,420,800 | 1/1969 | Haggis | 260/75 |
| 3,567,692 | 3/1971 | Haggis et al. | 260/75 |
| 5,258,482 | 11/1993 | Jacobs et al. | 528/49 |

OTHER PUBLICATIONS

"One Component Polyurethane Elastomers Based on Novel Polyaldimine", Polyurethanes World Congress 1993–Oct. 10–13, 1993, pp. 341–345, M. Aoki et al.

Huls–Vestamin A 139, Product Information Bulletin.

*Primary Examiner*—James J. Seidleck
*Assistant Examiner*—Duc Truong
*Attorney, Agent, or Firm*—Joseph C. Gil; Thomas W. Roy

[57] ABSTRACT

The present invention is directed to coating compositions which have long pot lives, may be rapidly cured under ambient conditions to provide coatings with improved optical properties and contain as binder a) a polyisocyanate component containing
   i) 5 to 100 % by weight of a monoallophanate and
   ii) 0 to 95% by weight of another polyisocyanate adduct, and
b) an aldimine based on the reaction product of a polyamine having 2 or more primary amino groups with an aldehyde corresponding to the formula:

$$O=CHCH(R_1)(R_2)$$

wherein $R_1$ and $R_2$ may be the same or different and represent optionally substituted hydrocarbon radicals, or $R_1$ and $R_2$ together with the β-carbon atom form a cycloaliphatic or heterocyclic ring, wherein components a) and b) are present in an amount sufficient to provide an equivalent ratio of isocyanate groups to aldimine groups of 0.5:1 to 20:1.

9 Claims, No Drawings

COATING COMPOSITIONS BASED ON ALDIMINES AND POLYISOCYANATES CONTAINING ALLOPHANATE GROUPS

BACKGROUND OF THE INVENTION

1. Field of the Invention

The present invention is directed to coating compositions having long pot lives and short dry times under ambient conditions in which the binder is based on aldimines and polyisocyanates which have improved compatibility with the aldimines.

2. Background of the Invention

Coating compositions which may be cured at room temperature are known. One-component coating compositions contain fully reacted polyurethanes as the binder. These compositions have the advantage that they are available as fully formulated systems which may be directly applied to suitable substrates without any preliminary steps except for mild stirring. Disadvantages of these systems are that large amounts of organic solvents are needed to reduce the viscosity of fully reacted, i.e., high molecular weight, polyurethanes. The coating compositions are cured by evaporation of the solvent which is objectionable from an environmental perspective. In addition, in order to solubilize the polyurethanes in organic solvents, they must be essentially linear polyurethanes. While such polyurethanes possess properties which are suitable for many applications, they do not provide certain properties, e.g., solvent resistance which may be obtained from crosslinked polyurethanes.

Two-component coating compositions are also known. These compositions come in two containers. The first contains a polyisocyanate, while the second contains an isocyanate-reactive component, generally a polyol. The components are not mixed until they are ready to be used. One advantage of these compositions is that because the components are not pre-reacted to form a high molecular weight polymer, a suitable processing viscosity can be achieved without the need for large amounts of organic solvents. In addition, higher functional components can be used to obtain highly crosslinked coatings which possess properties which surpass those possessed by one-component coatings.

The disadvantages of these compositions is that they cannot be applied without a preliminary mixing step in which it is critical that the components are mixed in the right proportions. In addition, special metering and mixing equipment is needed to conduct this process on a commercial scale. If the components are mixed in the wrong proportions, then the properties of the resulting coatings can be substantially affected. In addition, after the components are mixed they must be used in a timely fashion. If not, they continue to react until an unusable solid is obtained.

Coating compositions which possess the advantages of the known one- and two-component coating compositions without possessing their disadvantages may be prepared by blending the polyisocyanate adducts such as trimers and biurets with certain aldimines. However, coatings prepared from these known components are unacceptable due to their appearance. Further improvements are needed in clarity, gloss and distinctness of image (DOI) in order for these compositions to be useful in coating applications. These propedies are directly related to the compatibility between the polyisocyanate and the aldimine.

It is an object of the present invention to improve the clarity, gloss and DOI of coating compositions based on polyisocyanates and aldimines. This object may be achieved with coating compositions in which the polyisocyanate component is based on polyisocyanates having allophanate groups or mixtures of these polyisocyanates with other polyisocyanate adducts.

U.S. Pat. Nos. 3,420,800 and 3,567,692 disclose coating compositions containing polyisocyanates and either aldimines or kerimines. However, these patents do not teach that the compatibility of the binder components can be improved by the use of polyisocyanates containing allophanate groups.

SUMMARY OF THE INVENTION

The present invention is directed to coating compositions which have long pot lives, may be rapidly cured under ambient conditions to provide coatings with improved optical propedies and contain as binder a) a polyisocyanate component containing
   i) 5 to 100% by weight of a monoallophanate and
   ii) 0 to 95% by weight of another polyisocyanate adduct, and
b) an aldimine based on the reaction product of a polyamine having 2 or more primary amino groups with an aldehyde corresponding to the formula:

wherein $R_1$ and $R_2$ may be the same or different and represent optionally substituted hydrocarbon radicals, or $R_1$ and $R_2$ together with the β-carbon atom form a cycloaliphatic or heterocyclic ring, wherein components a) and b) are present in an amount sufficient to provide an equivalent ratio of isocyanate groups to aldimine groups of 0.5:1 to 20:1.

DETAILED DESCRIPTION OF THE INVENTION

In accordance with the present invention the term "monoallophanate" means a polyisocyanate containing one allophanate group and formed from two isocyanate molecules and 1 monoalcohol molecule, and the term "polyallophanate" means a polyisocyanate containing more than one allophanate group. The term "(cyclo)aliphatically bound isocyanate groups" means aliphatically and/or cycloaliphatically bound isocyanate groups.

In accordance with the present invention it has been discovered that polyisocyanates containing allophanate groups which are generated from monoalcohol have excellent compatibility with aldimines. Because of this compatibility, the resulting coatings have improved clarity, gloss and DOI when compared to coatings prepared from compositions which do not possess these allophanate groups. In addition to using the polyisocyanates containing allophanate groups as the only polyisocyanate component, these polyisocyanates may also be blended with other monomeric polyisocyanates, polyisocyanate adducts or NCO prepolymers to improve their compatibility with aldimines.

The polyisocyanates containing allophanate groups may be prepared by reacting monourethanes with monomeric diisocyanates at elevated temperatures to form allophanate groups. The monourethanes may be prepared in an initial step by reacting monomeric diisocyanates with monoalcohols or they may be prepared in situ by adding the monoalcohols to an excess of monomeric diisocyanates. Suitable processes for preparing these products are described in U.S. Pat. Nos. 4,160,080 and 3,769,318, the disclosures of which are herein incorporated by reference.

Examples of suitable diisocyanates to be used as starting materials for preparing the polyisocyanates containing allophanate groups include organic diisocyanates represented by the formula $$R(NCO)_2$$

wherein R represents an organic group obtained by removing the isocyanate groups from an organic diisocyanate having aromatically or (cyclo)aliphatically bound isocyanate groups and a molecular weight of 112 to 1,000, preferably 140 to 400. Preferred diisocyanates for the process according to the invention are those represented by the above formula wherein R represents a divalent aliphatic hydrocarbon group having 4 to 18 carbon atoms, a divalent cycloaliphatic hydrocarbon group having 5 to 15 carbon atoms, a divalent araliphatic hydrocarbon group having 7 to 15 carbon atoms or a divalent aromatic hydrocarbon group having 6 to 15 carbon atoms.

Examples of the organic diisocyanates which are particularly suitable for the process include 1,4-tetramethylene diisocyanate, 1,6-hexamethylene diisocyanate, 2,2,4-trimethyl,-1,6-hexamethylene diisocyanate, 1,12-dodecamethylene diisocyanate, cyclohexane-1,3- and -1,4-diisocyanate, 1-isocyanato-2-isocyanatomethyl cyclopentane, 1-isocyanato-3-isocyanatomethyl-3,5,5-trimethyl-cyclohexane (isophorone diisocyanate or IPDI), bis-(4-isocyanatocyclohexyl)-methane, 2,4'-dicyclohexylmethane diisocyanate, 1,3- and 1,4-bis(isocyanatomethyl)-cyclohexane, bis-(4-isocyanato-3-methyl-cyclohexyl)-methane, $\alpha,\alpha,\alpha',\alpha'$-tetramethyl-1,3- and/or-1,4-xylylene diisocyanate, 1-isocyanato-1-methyl- 4(3)-isocyanatomethyl cyclohexane, 2,4- and/or 2,6-hexahydrotoluylene diisocyanate, 1,3- and/or 1,4-phenylene diisocyanate, 2,4- and/or 2,6-toluylene diiso-cyanate, 2,4- and/or 4,4'-diphenylmethane diisocyanate, 1,5-diisocyanato naphthalene and mixtures thereof. Aromatic polyisocyanates containing 3 or more isocyanate groups such as 4,4',4"-triphenylmethane diiso-cyanate and polyphenyl polymethylene polyisocyanates obtained by phosgenating aniline/formaldehyde condensates may also be used. Preferred diisocyanates are 1,6-hexamethylene diisocyanate, isophorone diisocyanate and bis-(4-isocyanato-cyclohexyl)-methane. 1,6-hexamethylene diisocyanate (HDI)is especially preferred.

It is also possible in accordance with the present invention to use blends of the previously mentioned diisocyanates with monoisocyanates or polyisocyanates having 3 or more isocyanate groups, provided that the isocyanate groups are (cyclo)aliphatically bound.

Suitable monoalcohols which may be used to prepare the polyisocyanates containing allophanate groups include aliphatic, cycloaliphatic, araliphatic or aromatic monoalcohols. The monoalcohols may be linear, branched or cyclic, contain at least one carbon atom and have a molecular weight of up to 2500. The monoalcohols may optionally contain other hetero atoms in the form of, e.g., ether groups, ester groups, etc. However, the monoalcohols preferably do not contain hetero atoms other than the hydroxyl group itself. The molar ratio of monoalcohol to diisocyanate is about 0.01 to 0.5, preferably about 0.04 to 0.2. Preferred monoalcohols are hydrocarbon monoalcohol and monoalcohols containing ether groups.

The hydrocarbon monoalcohols preferably contain 1 to 36, more preferably 1 to 20 and most preferably 1 to 8 carbon atoms. Examples of suitable monoalcohols include methanol, ethanol, n-propanol, isopropanol, n-butanol, isobutanol and tert. butanol, n-pentanol, 2-hydroxy pentane, 3-hydroxy pentane, the isomeric methyl butyl alcohols, the isomeric dimethyl propyl alcohols, neopentyl alcohol, n-hexanol, n-heptanol, n-octanol, n-nonanol, 2-ethyl hexanol, trimethyl hexanol, cyclohexanol benzyl alcohol, phenol, the cresols, the xylenols, the trimethylphenols, decanol, dodecanol, tetradecanol, hexadecanol, octadecanol, 2,6,8-trimethylnonanol, 2-t-butyl-cyclohexanol, 4-cyclohexyl1-butanol, 2,4,6,-trimethyl benzyl alcohol, branched chain primary alcohols and mixtures thereof (which are available from Henkel under the Standamul trademark) and mixtures of linear primary alcohols (which are available from Shell under the Neodol trademark).

Preferred ether-containing monoalcohols include ethoxy methanol, methoxy ethanol, ethoxy ethanol, the isomeric methoxy or ethoxy propanols, the isomeric propoxy methanols and ethanols, the isomeric methoxy butanols, the isomeric butoxy methanols, furfuralcohol and other monoalcohols which have a molecular weight of up to 2500 and are based on ethylene oxide, propylene oxide and/or butylene oxide.

It is also possible in accordance with the present invention to use mixtures of the previously described monoalcohols.

The polyisocyanates containing allophanate groups may be blended with the previously described monomeric diisocyanates, with other polyisocyanate adducts or with NCO prepolymers to improve their compatibility with aldimines. These other polyisocyanate adducts include those containing isocyanurate, uretdione, biuret, urethane, allophanate, carbodiimide and/or oxadiazinetrione groups. The polyisocyanates adducts have an average functionality of 2 to 6 and an NCO content of 5 to 30% by weight.

1 ) Isocyanurate group-containing polyisocyanates which may be prepared as set forth in DE-PS 2,616,416, EP-OS 3,765, EP-OS 10,589, EP-OS 47,452, U.S. Pat. Nos. 4,288, 586 and 4,324,879. The isocyanato-isocyanurates generally have an average NCO functionality of 2.5 to 4.5, preferably 3 to 3.5 and an NCO content of 5 to 30%, preferably 10 to 25% and most preferably 15 to 25% by weight.

2) Uretdione diisocyanates which may be prepared by oligomerizing a portion of the isocyanate groups of a diisocyanate in the presence of a trialkyl phosphine catalyst and which may be used in admixture with other aliphatic and/or cycloaliphatic polyisocyanates, particularly the isocyanurate group-containing polyisocyanates set forth under (1) above.

3) Biuret group-containing polyisocyanates which may be prepared according to the processes disclosed in U.S. Pat. Nos. 3,124,605; 3,358,010; 3,644,490; 3,862,973; 3,906, 126; 3,903,127; 4,051,165; 4,147,714; or 4,220,749 by using co-reactants such as water, tertiary alcohols, primary and secondary monoamines, and primary and/or secondary diamines. These polyisocyanates preferably have an NCO content of 18 to 22% by weight and an average NCO functionality of 2.5 to 4.5, preferably 3 to 3.5.

4) Urethane group-containing polyisocyanates which may be prepared in accordance with the process disclosed in U.S. Pat. No. 3,183,112 by reacting excess quantities of polyisocyanates, preferably diisocyanates, with low molecular weight glycols and polyols having molecular weights of less than 400, such as trimethylol propane, glycerine, 1,2-dihydroxy propane and mixtures thereof. The urethane group-containing polyisocyanates have a most preferred NCO content of 12 to 20% by weight and an (average) NCO functionality of 2.5 to 4.5, preferably 2.5 to 3.

5) Allophanate group-containing polyisocyanates which may be prepared as described above from difunctional or higher functional, low or high molecular weight polyols as described in U.S. Pat. Nos. 3,769,318, 4,160,080 and 4,177, 342. The allophanate group-containing polyisocyanates have a most preferred NCO content of 12 to 21% by weight and an (average) NCO functionality of 2.5 to 4.5.

6) Carbodiimide group-containing polyisocyanates which may be prepared by oligomerizing di- or polyisocyanates in the presence of known carbodiimidization catalysts as described in DE-PS 1,092,007, U.S. Pat. No. 3,152,162 and DE-OS 2,504,400, 2,537,685 and 2,552,350.

7) Polyisocyanates containing oxadiazinetrione groups and containing the reaction product of two moles of a diisocyanate and one mole of carbon dioxide.

Preferred polyisocyanate adducts are the polyisocyanates containing isocyanurate groups, biuret groups or urethane groups.

Instead of using mixtures of polyisocyanates containing allophanate groups and polyisocyanate adducts which have been separately prepared, in certain cases it is possible to prepare these mixtures in one step. For example, mixtures of polyisocyanates containing allophanate groups and isocyanurate groups may be prepared by trimerizing the isocyanate starting material in the presence of trimerization catalysts and monoalcohols. Suitable catalysts and methods of the production of these polyisocyanate mixtures are disclosed, e.g., in U.S. Pat. Nos. 5,124,427, 5,208,334 and 5,235,018, the disclosures of which are herein incorporated by reference, and in copending applications U.S. Ser. Nos. 08/003,779, and 08/081,923, the disclosures of which are herein incorporated by reference.

In addition to mixtures of polyisocyanates containing allophanate groups and isocyanurate groups, it is also possible to directly prepare mixtures of polyisocyanates containing allophanate groups and biuret groups by biuretizing the isocyanate starting material in the presence of a biuretizing agent and a monoalcohol. It is less preferred to directly prepare polyisocyanates containing allophanate groups and urethane groups because in addition to forming allophanate groups from monourethanes, allophanate groups will also be formed from the polyisocyanates adducts containing more than one urethane group. This results in a substantial increase in the viscosity of the resulting product.

Preferred mixtures of polyisocyanates are those containing allophanate and isocyanurate groups or allophanate and biuret groups, more preferably allophanate and isocyanurate groups. The ratio of monoisocyanurate groups to monoallophanate groups present in these more preferred polyisocyanates is about 10:1 to 1:10, preferably about 5:1 to 1:7. These values may be determined by gel permeation chromatography (GPC) by determining the areas under the peaks for the monoisocyanurate and monoallophanate groups. The polyisocyanates according to the invention generally contain a total of less than 2, preferably less than 1% of free (unreacted) monomeric diisocyanates.

In addition to monomeric polyisocyanates and polyisocyanates adducts, the polyisocyanates containing allophanate groups may also be blended with NCO prepolymers to improve their compatibility with aldimines.

The NCO prepolymers, which may also be used as the polyisocyanate component in accordance with the present invention, are prepared from the previously described monomeric polyisocyanates or polyisocyanate adducts, preferably monomeric diisocyanates, and organic compounds containing at least two isocyanate-reactive groups, preferably at least two hydroxy groups. These organic compounds include high molecular weight compounds having molecular weights of 400 to about 6,000, preferably 800 to about 3,000, and optionally low molecular weight compounds with molecular weights below 400. The molecular weights are number average molecular weights ($M_n$) and are determined by end group analysis (NH number). Products obtained by reacting polyisocyanates exclusively with low molecular weight compounds are polyisocyanates adducts containing urethane groups and are not considered to be NCO prepolymers.

Examples of the high molecular weight compounds are polyester polyols, polyether polyols, polyhydroxy polycarbonates, polyhydroxy polyacetals, polyhydroxy polyacrylates, polyhydroxy polyester amides and polyhydroxy polythioethers. The polyester polyols, polyether polyols and polyhydroxy polycarbonates are preferred. Further details concerning the low molecular weight compounds and the starting materials and methods for preparing the high molecular weight polyhydroxy compounds are disclosed in U.S. Pat. No. 4,701,480, herein incorporated by reference.

These NCO prepolymers generally have an isocyanate content of about 0.5 to 30% by weight, preferably about 1 to 20% by weight, and are prepared in known manner by the reaction of the above mentioned starting materials at an NCO/OH equivalent ratio of about 1.05:1 to 10:1 preferably about 1.1:1 to 3:1. This reaction may take place in a suitable solvent which may optionally be removed by distillation after the reaction along with any unreacted volatile starting polyisocyanates still present. In accordance with the present invention NCO prepolymers also include NCO semi-prepolymers which contain unreacted starting polyisocyanates in addition to the urethane group-containing prepolymers.

In mixtures with monomeric polyisocyanates, polyisocyanate adducts or NCO prepolymers to provide improved compatibility, the polyisocyanates containing allophanate groups should be present in an amount of at least 5% by weight, preferably at least 25% by weight and more preferably at least 40% by weight, based on the solids content of the polyisocyanate component.

It is also possible in accordance with the present invention to use polyisocyanates containing allophanate groups and, e.g., isocyanurate groups, to compatibilize other polyisocyanate adducts or NCO prepolymers, provided that the resulting mixture contains the previously disclosed amounts of polyisocyanates containing allophanate groups.

Suitable aldimines for use in combination with the polyisocyanate mixtures include those prepared from an aldehyde and polyamines containing two or more, preferably 2 to 6 and more preferably 2 to 4, primary amino groups. The polyamines include high molecular weight amines having molecular weights of 400 to about 10,000, preferably 800 to about 6,000, and low molecular weight amines having molecular weights below 400. The molecular weights are number average molecular weights ($M_n$) and are determined by end group analysis (OH number). Examples of these polyamines are those wherein the amino groups are attached to aliphatic, cycloaliphatic, araliphatic and/or aromatic carbon atoms.

Suitable low molecular polyamines starting compounds include tetramethylene diamine, ethylene diamine, 1,2- and 1,3-propane diamine, 2-methyl-1,2-propane diamine, 2,2-dimethyl-1,3-propane diamine, 1,3- and 1,4-butane diamine, 1,3- and 1,5-pentane diamine, 2-methyl-1,5-pentane diamine, 1,6-hexane diamine, 1,7-heptane diamine, 1,8-octane diamine, 1,9-nonane diamine, 1,10-decane diamine, 1,11-dodecane diamine, 1-amino-3-aminomethyl-3,5,5-trimethyl cyclohexane, bis-(4-aminocyclohexyl)-methane, bis-(4-amino-3-methylcyclohexyl)-methane, 1,2- and/or 1,4-cyclohexane diamine, 1,3-bis(methylamino)-cyclohexane, 1,8-p-menthane diamine, hydrazine, hydrazides of semicarbazido carboxylic acids, bis-hydrazides, bis-semicarbazides, phenylene diamine, 2,4- and/or 2,6-toluylene diamine, 2,3- and/or 3,4-toluylene diamine, polyphenylene polymethylene polyamines of the kind obtained by the aniline/formaldehyde condensation reaction, N,N,N-tris(2-aminoethyl)-amine, guanidine, melamine, N-(2-aminoethyl)-1,3-propane diamine, 3,3'-diamino-benzidine, polyoxypropylene amines, polyoxyethylene amines, 2,4-bis-(4'-aminobenzyl)-aniline and mixtures thereof.

Preferred polyamines are 1-amino-3-aminomethyl-3,5,5-trimethyl-cyclohexane (isophorone diamine or IPDA), bis-(4-aminocyclohexyl)-methane, bis-(4-amino-3-methylcyclohexyl)-methane, 1,6-diaminohexane, 2-methyl pentamethylene diamine and ethylene diamine.

Suitable high molecular weight polyamines correspond to the polyhydroxyl compounds used to prepare the NCO prepolymers with the exception that the terminal hydroxy groups are converted to amino groups, either by amination or by reacting the hydroxy groups with a diisocyanate and subsequently hydrolyzing the terminal isocyanate group to an amino group. Preferred high molecular weight polyamines are amine-terminated polyethers such as the Jeffamine resins available from Texaco.

Suitable aldehydes are those corresponding to the formula

O=CHCH(R₁)(R₂)

wherein

R₁ and R₂ may be the same or different and represent optionally substituted hydrocarbon radicals, preferably containing 1 to 10, more preferably 1 to 6, carbon atoms, or R₁ and R₂ together with the β-carbon atom form a cycloaliphatic or heterocyclic ring.

Examples of suitable aldehydes include isobutyraldehyde, 2-ethyl hexanal, 2-methyl butyraldehyde, 2-ethyl butyraldehyde, 2-methyl valeraldehyde, 2,3-dimethyl valeraldehyde, 2-methyl undecanal and cyclohexane carboxaldehyde.

The aldimines may be prepared in known manner by reacting the polyamines with the aldehydes either in stoichiometric amounts or with an excess of aldehyde. The excess aldehyde and the water which is produced can be removed by distillation. The reactions may also be carried out in solvents, other than ketones. The solvents may also be removed by distillation after completion of the reaction.

The amounts of the polyisocyanates and aldimines are selected to provide an equivalent ratio of isocyanate groups to aldimine groups of 0.5:1 to 20:1, preferably 0.8:1 to 3:1 and more preferably 1:1 to 2:1.

In addition to the binder components, the coating compositions may also contain the known additives from coatings technology, such as fillers, pigments, softeners, high-boiling liquids, catalysts, UV stabilizers, anti-oxidants, microbiocides, algicides, dehydrators, thixotropic agents, wetting agents, flow enhancers, matting agents, anti-slip agents, aerators and extenders. The additives are chosen based on the requirements of the particular application and their compatibility with components a) and b). The coating compositions may be applied to the substrate to be coated by conventional methods such as painting, rolling, pouring or spraying.

The coating compositions according to the invention have good storage stability and provide coatings which have relatively fast dry times. The coatings are also characterized by high hardness, elasticity, very good resistance to chemicals, high gloss, good weather resistance, good environmental etch resistance and good pigmenting qualities.

It is believed that the combination of fast dry times and good storage stability is due to the fact that water catalyzes the reaction between the polyisocyanate and the aldimine. While the prior art indicates that the curing mechanism takes place by hydrolyzing the aldimine to the amine which then reacts with the isocyanate. This is not the mechanism which takes place in accordance with the present invention. This is easily confirmed by the fact that aldehydes are not release during the curing reaction. The direct reaction between the aldimines and polyisocyanates does not take place in the absence of catalysts such as atmospheric moisture, which accounts for the excellent storage stability. However, after the coating composition has been applied to a suitable substrate, the same components which did not react when present in admixture in storage, rapidly react to form a coating. The reason for this phenomenon is believed to be the catalytic effect of atmospheric moisture.

The invention is further illustrated, but is not intended to be limited by the following examples in which all parts and percentages are by weight unless otherwise specified.

EXAMPLES

Polyisocyanate 1

To a 500 ml 3-neck flask equipped with a gas bubbler, mechanical stirrer, thermometer and condenser were added 301.7 parts of hexamethylene diisocyanate and 13.3 parts of 1-butanol. Dry nitrogen was bubbled through the stirred reaction mixture while it was heated at 60° C. When the urethane reaction was complete (about 1 hour), the temperature was raised to 90° C. To the reaction mixture at 90° C. were added 0.214 parts of a 4.4% solution of trimethylbenzylammonium hydroxide dissolved in 1-butanol. The reaction temperature was maintained at 90° to 100° C. When the reaction mixture reached NCO contents of 40.1% and 37.0%, an additional 0.12 parts of the catalyst solution was added. When the reaction mixture reached an NCO content of 34.8%, the reaction was stopped by adding 0.214 parts of di-(2-ethylhexyl) phosphate. The excess monomer was removed by thin film evaporation to provide an almost colorless, clear liquid having a viscosity of 630 mPa.s (25° C.), an NCO content of 19.7%, and a free monomer (HDI) content of 0.35%. The yield was 48.6%. The yield was calculated by determining the percentage of free hexamethylene diisocyanate in the product prior to distillation.

Polyisocyanate 2

An isocyanurate group-containing polyisocyanate prepared from 1,6-hexamethylene diisocyanate and having an isocyanate content of 21.6%, a content of monomeric diisocyanate of <0.2% and a viscosity at 20° C. of 3000 mPa.s (available from Miles Inc. as Desmodur N 3300).

Polyisocyanate 3

A biuret group-containing polyisocyanate prepared from 1,6-hexamethylene diisocyanate and having an isocyanate content of about 23%, a content of monomeric diisocyanate of <0.7% and a viscosity at 25° C. of 1300–2200 mPa.s (available from Miles Inc. as Desmodur N 3200).

Polyisocyanate 4

An isocyanurate group-containing polyisocyanate present as a 70% solution in 1:1 blend of propylene glycol monomethyl ether acetate and xylene, prepared from isophorone diisocyanate, and having, based on the weight of the solution, an isocyanate content of 11.7% by weight, a content of monomeric diisocyanate of <0.5% and a viscosity at 20° C. of 1300 to 2700 mPa.s (available from Miles Inc. as Desmodur Z 4370).

Polyisocyanate 5

To a 2 liter 3-neck flask equipped with a gas bubbler, mechanical stirrer, thermocouple and condenser, were added 1110 parts of isophorone diisocyanate and 68 parts of n-butanol. The stirred mixture was heated for 2 hours at 70° C. while dry nitrogen was bubbled through the reaction mixture. The temperature of the urethane reaction mixture was then raised to 80° C. To the reaction mixture at 80° C. were added dropwise 10.84 parts (300 ppm) of a catalyst solution, which was prepared by reducing a 40% solution of benzyltrimethyl ammonium hydroxide in methanol to a solids content of 5% by the addition of n-butanol. When the reaction mixture attained an NCO content of 25.90%, the reaction was stopped by adding 2.6 parts of a 25% solution of di-(2-ethylhexyl)-phosphate (586 ppm) in hexamethylene diisocyanate. The excess monomer was removed by thin film evaporation to provide a pale yellow solid having a viscosity of 7667 mPa.s at 80° C., an NCO content of 14.2% and a free monomer (IPDI) content of 0.29%. The actual yield was 42.4% and the molar ratio of monoisocyanurate to monoallophanate was 1:4.8.

Polyisocyanate 6

This polyisocyanate was prepared following the procedure of Example 1 with the exception that 26.2 parts of isocetyl alcohol was used in place n-butanol and the reaction was conducted at 120° C. The reaction was terminated by the addition of the catalyst poison when the NCO content was 28.5%. After removal of unreacted monomer, the resulting product was an almost colorless, clear liquid having a viscosity of 375 mPa.s (25° C.), an NCO content of 14.3%, and a free monomer (HDI) content of 0.05%.

Polyisocyanate 7

To a reactor equipped with a gas bubbler, stirrer, thermometer and dropping funnel were added 100 parts of hexamethylene diisocyanate (HDI). The stirred HDI was heated to 120° C. while dry nitrogen was bubbled through the HDI. To the stirred HDI was added 3.0 parts of n-butanol containing 0.0026 parts of trimethylbenzyl ammonium hydroxide at such a rate that the 120° C. temperature was maintained. After the addition was complete the reaction mixture was held at 120° C. for an additional 15 minutes followed by the addition of 0.0026 parts of di-(2-ethylhexyl) phosphate to terminate the reaction. The reaction mixture had an NCO content of 42.0%. The excess monomer was removed by thin film evaporation to provide an almost colorless, clear liquid having a viscosity of 250 mPa.s (25° C.), an NCO content of 20.9%, and a free monomer (HDI) content of 0.2%.

Polyisocyanate 8

To a reactor equipped with a gas bubbler, stirrer, thermometer and dropping funnel were added 100 parts of hexamethylene diisocyanate (HDI). The stirred HDI was heated to 120° C. while dry nitrogen was bubbled through the HDI. To the stirred HDI was added 10.0 parts of n-butanol containing 0.0032 parts of trimethylbenzyl ammonium hydroxide at such a rate that the 120° C. temperature was maintained. After the addition was complete the reaction mixture was held at 120° C. for an additional 15 minutes followed by the addition of 0.0032 parts of di-(2-ethylhexyl) phosphate to terminate the reaction. The reaction mixture had an NCO content of 30.5%. The excess monomer was removed by thin film evaporation to provide an almost colorless, clear liquid having a viscosity of 380 mPa.s (25° C.), an NCO content of 17.7%, and a free monomer (HDI) content of 0.39%.

Polyisocyanate 9

A biuret group-containing polyisocyanate prepared from 1,6-hexamethylene diisocyanate and having an isocyanate content of about 22%, a content of monomeric diisocyanate of <0.7% and a viscosity at 25° C. of 5000–10,000 mPa.s (available from Miles Inc. as Desmodur N 100).

Aldimine 1

The aldimine of bis-(4-aminocyclohexyl)-methane and isobutraidehyde was prepared by initially charging 1514.3 parts (21 equivalents) of isobutraldehyde and then slowly charging 2104.0 parts (20 equivalents) of bis-(4-aminocyclohexyl)-methane over a period of thirty minutes to avoid an exotherm. After the addition of the diamine the reaction mixture was stirred for one hour. At this time stirring was stopped and water was allowed to settle to the bottom of the reactor. As much water as possible was drained from the bottom of the reactor. The reaction mixture was then heated to 100° C. to remove excess isobutraldehyde. While maintaining a temperature of 100° C., a vacuum of approximately 20 mm Hg was applied to remove any final traces of aldehyde. Thereafter the vacuum was increased to 1 mm Hg to remove water until the water content was less than 0.05% (approximately 1 to 3 hours.) The aldimine had a viscosity of 100 mPa.s at 25° C., an equivalent weight of 159.3, an APHA color of 70, a purity as determined by GPC of 93.5% and a water content of less than 0.05%.

Aldimine 2

The aldimine of 2-methyl pentamethylene diamine and isobutyraldehyde was prepared using the procedure described for aldimine 1.

Aldimine 3

The aldimine of an amine-terminated polyether, MW 400, prepared by aminating polypropylene glycol (available from Texaco as Jeffamine D-400) and isobutyraldehyde was prepared using the procedure described for aldimine 1.

Aldimine 4

The aldimine of an amine-terminated polyether, MW 2000, prepared by aminating polypropylene glycol (available from Texaco as Jeffamine D-2000) and isobutyraldehyde was prepared using the procedure described for aldimine 1.

Aldimine 5

The aldimine of an amine-terminated polyether, MW 5000, prepared by aminating polypropylene triol (available from Texaco as Jeffamine T-5000) and isobutyraldehyde was prepared using the procedure described for aldimine 1.

Aldimine 6

The aldimine of hexamethylene diamine and isobutyraldehyde was prepared using the procedure described for aldimine 1.

Aldimine 7

The aldimine of bis-(4-diphenylmethane)-diamine and isobutyraldehyde was prepared using the procedure described for aldimine 1.

Performance of Compatibility Testing for Table 1

To perform the initial compatibility testing, 1 to 1 volume amounts of the neat polyisocyanate resins were combined with the neat aldimine resins and mixed by hand for one minute. The mixtures were evaluated for compatibility based on appearance using the criteria of immiscibility and cloudiness as indicators. The mixtures were rated immediately, after standing for one hour and after standing for 24 hours. In each case, no changes were seen from the initial ratings. The results are set forth in the following tables. A rating of excellent means that the components mixed together with minimal effort and with no turbidity or cloudiness. A rating of good means that the components mixed together with more than minimal effort, but with no turbidity or cloudiness. A rating of fair means that the components mixed together with more than minimal effort and the mixture was turbid or cloudy. A rating of poor means that the components were either immiscible or that more than minimal effort was needed to mix the components and the resulting mixture was extremely turbid or cloudy.

TABLE 1

Resin Compatibility of Aldimines with Allophanate and non-Allophanate

| Polyisocyanates | ald 1 | ald 2 | ald 3 | ald 4 | ald 5 | ald 6 | ald 7 |
|---|---|---|---|---|---|---|---|
| Polyiso 1 | good | good | good | fair | fair | good | good |
| Polyiso 2 (Comp) | poor | poor | | | | | poor |
| Polyiso 3 (Comp) | poor | poor | | | | | poor |
| Polyiso 4 (Comp) | poor | fair | | | | | poor |
| Polyiso 5 | good | good | | | | | good |
| Polyiso 6 | excel | excel | | | | | excel |
| Polyiso 7 | good | good | | | | | good |
| Polyiso 8 | good | good | | | | | good |
| Polyiso 9 (Comp) | poor | poor | | | | | poor |

Table 1 demonstrates that allophanate modified polyisocyanates are more compatible with aldimine resins than polyisocyanates which do not contain allophanate groups.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A coating composition which has a long pot life, may be rapidly cured under ambient conditions to provide coatings with improved optical properties and contain as binder
   a) a polyisocyanate component containing
      i) 5 to 100% by weight of a monoallophanate and
      ii) 0 to 95% by weight of another polyisocyanate adduct, and
   b) an aldimine based on the reaction product of a polyamine having 2 or more primary amino groups with an aldehyde corresponding to the formula:

$$O=CHCH(R_1)(R_2)$$

wherein $R_1$ and $R_2$ may be the same or different and represent hydrocarbon radicals, or $R_1$ and $R_2$ together with the β-carbon atom form a cycloaliphatic or heterocyclic ring,
   wherein components a) and b) are present in an amount sufficient to provide an equivalent ratio of isocyanate groups to aldimine groups of 0.5:1 to 20:1.

2. The coating composition of claim 1 wherein component ai) is present in an amount of at least 25% by weight.

3. The coating composition of claim 1 wherein component a) is a polyisocyanate blend containing monoisocyanurate groups and monoallophanate groups in a ratio of 10:1 to 1:10.

4. The coating composition of claim 3 wherein said polyisocyanate blend is prepared from 1,6-hexamethylene diisocyanate.

5. A coating composition which has a long pot life, may be rapidly cured under ambient conditions to provide coatings with improved optical properties and contain as binder
   a) a polyisocyanate component containing
      i) 5 to 100% by weight of a monoallophanate and
      ii) 0 to 95% by weight of another polyisocyanate adduct, and
   b) an aldimine based on the reaction product of a polyamine having 2 or more primary amino groups with an aldehyde corresponding to the formula:

$$O=CHCH(R_1)(R_2)$$

wherein $R_1$ and $R_2$ may be the same or different and represent hydrocarbon radicals containing 1 to 6 carbon atoms,
   wherein components a) and b) are present in an amount sufficient to provide an equivalent ratio of isocyanate groups to aldimine groups of 0.5:1 to 20:1.

6. The coating composition of claim 5 wherein component ai) is present in an amount of at least 25% by weight.

7. The coating composition of claim 5 wherein component a) is a polyisocyanate blend containing monoisocyanurate groups and monoallophanate groups in a ratio of 10:1 to 1:10.

8. The coating composition of claim 7 wherein said polyisocyanate blend is prepared from 1,6-hexamethylene diisocyanate.

9. The coating composition of claim 5 wherein said aldehyde comprises isobutyraldehyde or 2-ethyl hexanal.

\* \* \* \* \*